US009155177B2

(12) United States Patent
Kikuchi

(10) Patent No.: US 9,155,177 B2
(45) Date of Patent: Oct. 6, 2015

(54) DATA COMMUNICATION SYSTEM AND RADIATION IMAGE CAPTURING SYSTEM

(71) Applicant: Konica Minolta, Inc., Tokyo (JP)

(72) Inventor: Ryouhei Kikuchi, Hachioji (JP)

(73) Assignee: KONICA MINOLTA, INC. (JP)

( * ) Notice: Subject to any disclaimer, the term of this patent is extended or adjusted under 35 U.S.C. 154(b) by 211 days.

(21) Appl. No.: 13/864,755

(22) Filed: Apr. 17, 2013

(65) Prior Publication Data

US 2013/0279660 A1 Oct. 24, 2013

(30) Foreign Application Priority Data

Apr. 20, 2012 (JP) ................................. 2012-096260

(51) Int. Cl.
H05G 1/08 (2006.01)
H04W 72/04 (2009.01)
H04W 72/08 (2009.01)
A61B 6/00 (2006.01)

(52) U.S. Cl.
CPC ................ *H05G 1/08* (2013.01); *A61B 6/4405* (2013.01); *A61B 6/548* (2013.01); *A61B 6/56* (2013.01); *A61B 6/566* (2013.01); *A61B 6/586* (2013.01); *H04W 72/082* (2013.01)

(58) Field of Classification Search
CPC ..... H05G 1/08; H04W 72/082; A61B 6/4405; A61B 6/548; A61B 6/56; A61B 6/566
USPC ......... 378/91, 98.8; 250/370.09; 455/39, 500, 455/501
See application file for complete search history.

(56) References Cited

U.S. PATENT DOCUMENTS

| | | | | | |
|---|---|---|---|---|---|
| 5,675,629 | A | * | 10/1997 | Raffel et al. | 455/552.1 |
| 5,911,120 | A | * | 6/1999 | Jarett et al. | 455/417 |
| 6,487,414 | B1 | * | 11/2002 | Tanay et al. | 455/450 |
| 6,754,499 | B1 | * | 6/2004 | Smith | 455/450 |
| 7,634,277 | B2 | * | 12/2009 | Jin et al. | 455/452.2 |
| 7,677,798 | B2 | * | 3/2010 | Ohnona et al. | 378/191 |
| 7,737,427 | B2 | * | 6/2010 | Kito et al. | 250/580 |
| 7,864,923 | B2 | * | 1/2011 | Ohta et al. | 378/102 |
| 7,873,145 | B2 | * | 1/2011 | Liu et al. | 378/98.8 |
| 8,021,045 | B2 | * | 9/2011 | Foos et al. | 378/198 |
| 8,031,837 | B2 | * | 10/2011 | Spahn | 378/91 |

(Continued)

FOREIGN PATENT DOCUMENTS

| | | | |
|---|---|---|---|
| JP | 6-342099 A | 12/1994 |
| JP | 9-73144 A | 3/1997 |

(Continued)

*Primary Examiner* — Allen C. Ho
(74) *Attorney, Agent, or Firm* — Cantor Colburn LLP

(57) ABSTRACT

A data communication system and a radiation image capturing system are described. According to one implementation, a data communication system includes a wireless terminal; an access point; and a channel determination section. The channel determination section carries out calculation processing for calculating an influence rate as a score for each of a plurality of channels, and determines a channel having the smallest calculated score to be a channel used, and classifies the influence rate by the interfering radio wave into a plurality of zones, sets the score in each of the zones so that the value of the score is higher as transmission/receiving of the data between the wireless terminal and the access point of the system becomes more difficult when the interfering radio wave having the strength of the zone exists, adds the scores of each zone, and calculates the score.

5 Claims, 6 Drawing Sheets

(56) References Cited

U.S. PATENT DOCUMENTS

| | | | |
|---|---|---|---|
| 8,053,727 B2 * | 11/2011 | Nishino et al. | 250/336.1 |
| 8,229,202 B2 * | 7/2012 | Kito et al. | 382/132 |
| 8,295,439 B2 * | 10/2012 | Yonekawa | 378/116 |
| 8,306,526 B2 * | 11/2012 | Yonezawa | 455/423 |
| 8,311,488 B2 * | 11/2012 | Furman et al. | 455/69 |
| 8,401,150 B2 * | 3/2013 | Watanabe | 378/114 |
| 8,428,012 B2 * | 4/2013 | Tateson et al. | 370/329 |
| 8,532,686 B2 * | 9/2013 | Schmidt et al. | 455/513 |
| 8,781,075 B2 * | 7/2014 | Liu et al. | 378/114 |
| 8,818,437 B2 * | 8/2014 | Chan et al. | 455/513 |
| 8,848,872 B2 * | 9/2014 | Lee | 378/91 |
| 8,976,930 B2 * | 3/2015 | Ishizaka | 378/98.2 |

FOREIGN PATENT DOCUMENTS

| | | |
|---|---|---|
| JP | 2006-58124 A | 3/2006 |
| JP | 4519535 B2 | 5/2010 |

* cited by examiner

DATA COMMUNICATION SYSTEM AND RADIATION IMAGE CAPTURING SYSTEM

CROSS REFERENCE TO RELATED APPLICATIONS

The present invention claims priority under 35 U.S.C. §119 to Japanese Application No. 2012-096260 filed Apr. 20, 2012, the entire content of which is incorporated herein by reference.

BACKGROUND

1. Field of the Invention

The present invention relates to a data communication system and a radiation image capturing system and particularly to a data communication system for carrying out transmission/receiving of data between a wireless terminal and an access point and to a radiation image capturing system utilizing such system.

2. Description of Related Art

Recently, various types of technology concerning wireless communication of data or the like carried out by use of, for example, IEEE 802.11 method between a wireless terminal and an access point (also referred to as a base unit, base station, station, or the like) in a separated position by way of a wireless local area network (wireless LAN, or also referred to as WLAN) have been developed (e.g., refer to Japanese Patent No. 4519535)

Moreover, data communication technology by way of wireless LAN has been expanding not only in the conventional wireless communication in the computer network but also in a wide range of fields such as wireless communication between wireless terminals such as a computer, audio equipment, visual equipment, and a game machine. In addition, field of utilization has been expanding, for example, into the field of medicine.

In the field of medicine, in a case where a radiation image is captured for the purpose of diagnosis or the like, a screen film using silver salt or the like has been conventionally used. However, in recent years, a radiation image capturing device for detecting radiation such as X-ray irradiated through a subject by photodiode or the like and acquiring a radiation image as a digitalized image data has been developed.

There is a so-called direct-type radiation image capturing device which generates an electric charge according to the dose of irradiated radiation by a detecting element and converts the electric charge thus generated into an electric signal (that is, image data, same shall be applied below) and a so-called indirect-type radiation image capturing device which converts irradiated radiation into a light having other wavelength such as a visible light by way of a scintillator or the like and then generates an electric charge by a photoelectric conversion element such as a photodiode according to the energy of the converted and irradiated light to convert the electric charge into an electric signal. In the present invention, a detecting element of the direct-type radiation image capturing device and a photoelectric conversion element of the indirect-type radiation image capturing device will be collectively referred to as a radiation detecting element.

Such type of a radiation image capturing device has been known as a flat panel detector (FPD) and conventionally has been configured as a dedicated machine formed as one with a supporting platform (e.g., refer to Japanese Published Unexamined Patent Application No. H9-73144). However, in recent years, a portable radiation image capturing device including a case in which the radiation detecting element and the like are stored so as to be able to be transported has been developed and practically used (for example, refer to Japanese Published Unexamined Patent Application No. 2006-058124 and Japanese Published Unexamined Patent Application No. H6-342099).

Specifically, because a portable radiation image capturing device can be carried to any location, in a case where radiation image of a patient who cannot move to a capturing chamber is captured, the radiation image capturing device can be brought into the patient's room and used by placing the device to the patient's body or sandwiching the device between a bed and the patient's body. Then, radiation is irradiated through the subject to the radiation image capturing device in such a condition to carry out capturing of a radiation image.

In this case, when image data or the like acquired by the radiation image capturing device is transmitted to an external device, if it is configured that the image data or the like is transmitted by, for example, a wired method in which a cable is connected to the radiation image capturing device, there is a possibility that the cable might entangle around an operator such as a radiology technician. Therefore, transmission of the image data or the like is carried out by a wireless method in many cases.

In such case, data communication technology by way of the above-mentioned wireless LAN is often utilized. If the wireless LAN is used, there is an advantage that configuration for transmission or the like of the image data or the like can be easily established since its standards are already determined and it is technologically matured.

However, on the other hand, technology of the wireless LAN has been widely spread as mentioned above and used by various wireless terminals. Therefore, there is a possibility that transmission/receiving of data have been already frequently carried out between various wireless terminals and access points even in the patient's room or the like.

Then, in a case where the above-mentioned portable type radiation image capturing device is brought into the patient's room in such a condition and data communication between the radiation image capturing device and an external device (to be precise, between an access point to which the external device is connected and a radiation image capturing device) is carried out, there is a possibility that radio waves from other wireless terminals become an interfering radio wave and prevent data communication between the radiation image capturing device and the external device.

Therefore, in a case where data communication is carried out by way of the wireless LAN, it becomes necessary to carry out data communication by selecting a channel which is not influenced by the interfering radio wave, or a channel which is least influenced by the interfering radio wave and by using such a channel. Moreover, concerning the influence by the interfering radio wave, in a case where wireless communication is carried out by use of a channel of the wireless LAN, it becomes necessary to give consideration to the influence of not only the interfering radio wave which uses the same channel but also the influence of so-called leakage of the interfering radio wave to the channel from a channel in the vicinity of the channel.

Therefore, in a data communication device or the like described in the Japanese Patent No. 4519535, a technology has been proposed that the number of access points which are carrying out communication by use of a channel is added and concerning a channel other than this channel, a coefficient, which decreases as the other channels become farther from the channel, is multiplied to the number of access points using the other channel, addition with weighting is carried out, and based on the values thus calculated, utilization condition of the channel is judged.

Meanwhile, 13 channels are provided to the wireless LAN of so-called 2.4 GHz band. In the band frequency of the 2.4 GHz, a radio wave used in a certain channel leaks out to another channel as mentioned above and the radio wave relatively strongly influences a channel in the vicinity of the channel using the radio wave. Therefore, it is said that in order to carry out communication in the 2.4 GHz band without interfering each other by the radio waves, only 3 or 4 channels among the 13 channels can be practically used.

In a wireless LAN of the 2.4 GHz band frequency, since the radio wave relatively strongly influences a channel in the vicinity of the channel using the radio wave as mentioned above, it becomes necessary to judge the utilization condition of a radio wave in a channel which is to be used, giving a consideration to the influence of the interfering radio wave from a channel which is relatively far from the channel to be used, similarly to a data communication device described in Japanese Patent No. 4519535.

However, it is known that in a case where wireless LAN is used in a so-called 5 GHz band frequency, influence by a radio wave reaches only within the channel used for the radio wave and channels adjacent to the channel and does not expand any further (e.g., refer to later-described FIG. 5). Therefore, it becomes hardly necessary to give consideration to the influence by the radio wave used in a channel which is farther than the channels adjacent to the channel, unlike the data communication device or the like described in the above-mentioned Japanese Patent No. 4519535.

Moreover, according to a study by the inventors of the present invention, it was understood that in a judgment of which channel to select at the time when a channel without influence by the interfering radio wave or with least influence is selected, although the level of the interfering radio wave is an important factor as described in the data communication technology described in the above-mentioned Japanese Patent No. 4519535 (that is, the number of access points utilizing the channel or the other channels), another important factor contributes to the selection.

It became known that if this important factor functions in wireless data communication, the influence is not limited to the influence by other interfering radio waves such as lowered communication speed of data or deteriorated S/N ratio of data caused by the noise which superimposes on the transmitted data, but in the worst case, there is a possibility that data communication cannot be carried out.

SUMMARY

The present invention has been made in consideration of the above-mentioned problems and aims at providing a data communication system which can accurately select a channel for communication with the least influence by an interfering radio wave by another wireless terminal when, for example, carrying out transmission or receiving of data between a wireless terminal such as a radiation image capturing device and an access point, and a radiation image capturing system utilizing such data communication system.

According to an aspect of the present invention there is provided a data communication system and a radiation image capturing system including:

a wireless terminal including a wireless communication section which carries out wireless transmission/receiving of data;

an access point which carries out wireless transmission/receiving of the data with the wireless communication section of the wireless terminal; and a channel determination section which is connected to the access point and which determines a channel to be used when carrying out the wireless transmission/receiving of the data between the wireless terminal and the access point, wherein the channel determination section, carries out calculation processing for quantifying the influence rate of an interfering radio wave and calculating the influence rate as a score for each of a plurality of channels by switching a target channel, for a case where data communication is carried out by use of a radio wave of the channel, on the basis of the influence rate of the interfering radio wave in the target channel among a plurality of usable channels, and determines a channel having the smallest calculated score to be a channel used for wireless transmission/receiving of the data between the wireless terminal and the access point, and classifies the influence rate by the interfering radio wave in the target channel into a first zone where strength of the interfering radio wave is strong enough to cause the access point of the system and an access point of another system to recognize existence of each other, a second zone where the strength of the interfering radio wave is weak enough to be regarded as noise, and a third zone where the strength is intermediate between the first zone and the second zone, sets the score in each of the zones so that the value of the score is higher as transmission/receiving of the data between the wireless terminal and the access point of the system becomes more difficult when the interfering radio wave having the strength of the zone exists, adds the scores of each zone, and calculates the score.

BRIEF DESCRIPTION OF THE DRAWINGS

The present invention will become more fully understood from the detailed description given hereinbelow and the appended drawings, and thus are not intended to define the limits of the present invention, and wherein.

DETAILED DESCRIPTION OF PREFERRED EMBODIMENTS

Hereinafter, an embodiment of a data communication system and a radiation image capturing system according to the present invention will be explained with reference to the figures.

Figure 1:
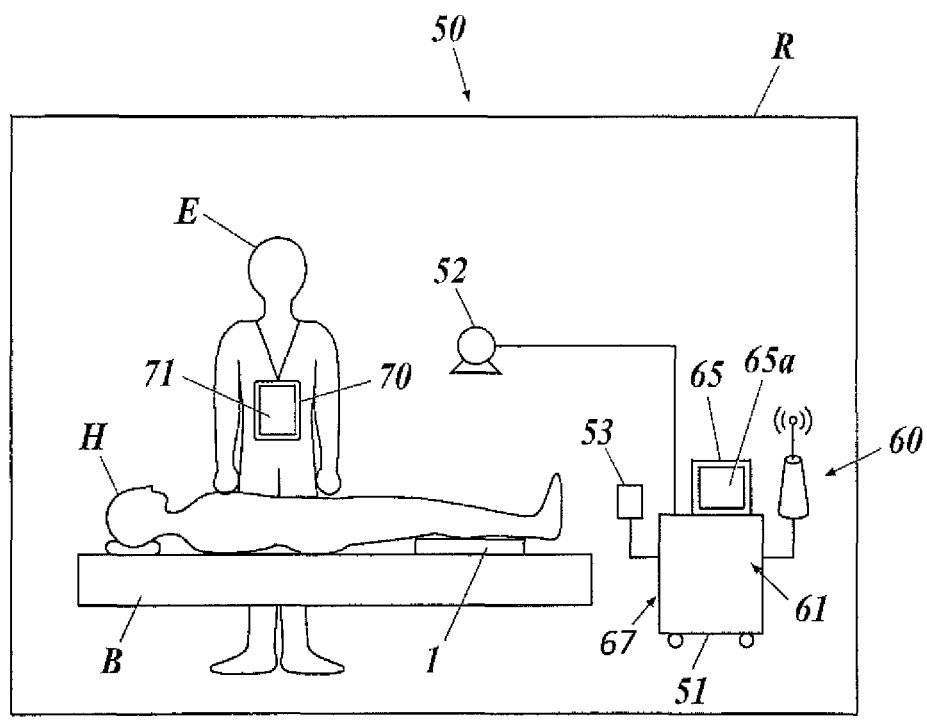
FIG. 1 is a view showing a configuration example of a radiation image capturing system as an example of a data communication system.

FIG. 1 is a view showing a configuration example of a radiation image capturing system 50 as an example of a data communication system. Note that in the present embodiment, an example where the data communication system is applied to the radiation image capturing system 50 will be explained. However, the data communication system according to the present invention can be applied to a system other than the radiation image capturing system 50 if the system carries out data communication by way of a wireless method and is not limited to a case where the data communication system is applied to the radiation image capturing system 50.

In the present embodiment, a radiation image capturing device 1 which detects radiation irradiated through a subject with a plurality of radiation detecting elements to acquire image data D functions as a wireless terminal and a channel used when wireless data communication is carried out between the radiation image capturing device 1 and a portable access point 60 is selected and determined.

Figure 2:
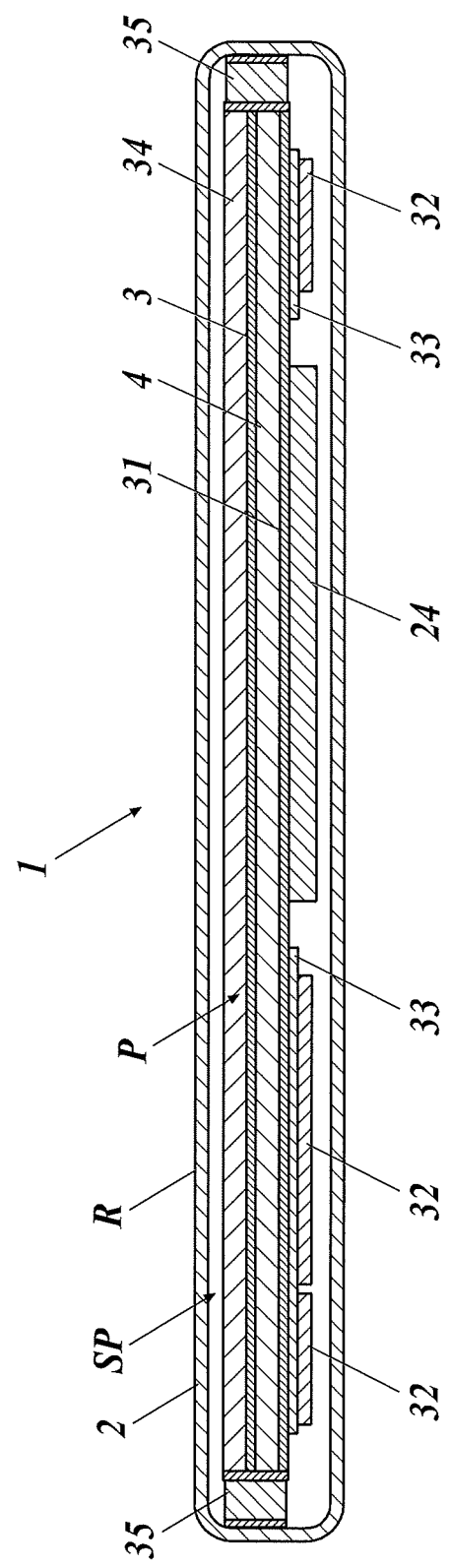
FIG. 2 is a cross-sectional view of a radiation image capturing device.

Hereinafter, configuration or the like of the radiation image capturing device 1 as a wireless terminal will be explained first. FIG. 2 is a cross-sectional view of the radiation image capturing device 1.

The radiation image capturing device 1 is configured by storing a sensor panel SP including a scintillator 3, a substrate 4, or the like inside a case 2 having a radiation incidence surface R being a surface to which radiation is irradiated, as shown in FIG. 2, and is a portable type. Moreover, although not shown in FIG. 2, an antenna device 41 (refer to later-described FIG. 3), which is a wireless communication section for carrying out wireless transmission/receiving of data between an external device such as a later-described console 65 or a mobile terminal 70 (refer to FIG. 1), is provided to the case 2 of the radiation image capturing device 1.

As shown in FIG. 2, a base 31 is provided inside the case 2 and on the radiation incidence surface R side of the base 31 (hereinafter simply referred to as an upper surface side), the substrate 4 is provided via an unillustrated thin lead panel or the like. Then, on an upper surface side of the substrate 4, the scintillator 3 is provided on a scintillator substrate 34 and the scintillator 3 is provided to face the substrate 4 side.

Figure 3:
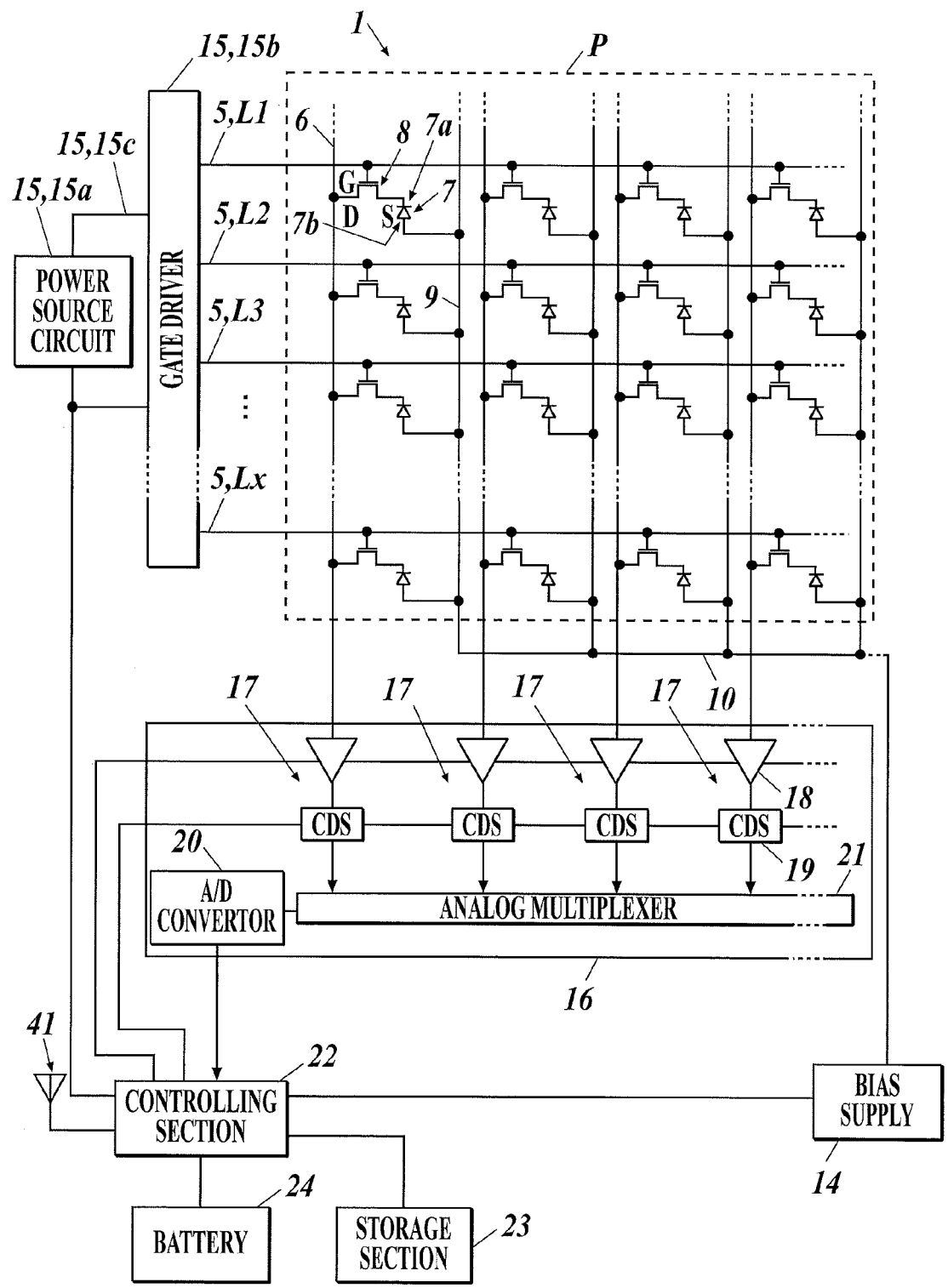
FIG. 3 is a block diagram showing an equivalent circuit of the radiation image capturing device.

Note that in the present embodiment, a case will be explained where the radiation image capturing device 1 is a so-called indirect type radiation image capturing device which includes the scintillator 3, converts the irradiated radiation into a light having other wavelength, such as a visible light, and irradiates the light to each of radiation detecting elements 7 as shown in FIG. 3. However, the radiation image capturing device 1 may be a so-called direct type radiation image capturing device which directly detects the radiation with the radiation detecting elements 7 without a scintillator or the like.

On a lower surface side of the base 31, a PCB substrate 33 on which electronic components 32 or the like are provided, a battery 24, or the like are attached. Thus, the sensor panel SP is configured by the base 31, the substrate 4, and the like. Moreover, in the present embodiment, a shock-absorbing material 35 is provided between the sensor panel SP and a side surface of the case 2.

Here, a circuit configuration of the radiation image capturing device 1 will be explained. FIG. 3 is a block diagram showing an equivalent circuit of the radiation image capturing device.

On an upper surface of the substrate 4 of the radiation image capturing device 1 (that is, a surface facing the scintillator 3), a plurality of scanning lines 5 and a plurality of signal lines 6 are provided to cross each other. Moreover, in each of small regions divided by the plurality of scanning lines 5 and the plurality of signal lines 6, a radiation detecting element 7 is provided.

Thus, in the radiation image capturing device 1, a plurality of radiation detecting elements 7 are aligned two-dimensionally (in a matrix manner) and an entire area where the plurality of radiation detecting elements 7 are provided, that is, an area shown by the dashed-dotted lines in FIG. 3, is a detection section P. In the present embodiment, photo diode is used as the radiation detecting element 7. However, another radiation detecting element such as, for example, photo transistor, may be used as the radiation detecting element 7.

A first electrode 7a of each of the radiation detecting elements 7 is connected to a source electrode 8S (refer to "S" in FIG. 3) of a TFT 8 being a switching section. Moreover, a drain electrode 8D and a gate electrode 8G (refer to "D" and "G" in FIG. 3) of the TFT 8 are connected to the signal line 6 and the scanning line 5 respectively.

In addition, in the present embodiment, as shown in FIG. 3, one bias line 9 is provided to a row of the radiation detecting element 7 to be connected to a second electrode 7b of each of the radiation detecting element 7, and the bias line 9 is bound at a position outside of the detection section P of the substrate 4 by a wire connection 10. Then, the wire connection 10 is connected to a bias supply 14 and a reverse bias voltage is applied from the bias supply 14 to the second electrodes 7b of each of the radiation detecting elements 7 via the wire connection 10 and each of the bias lines 9.

In the meantime, each of the scanning lines 5 is respectively connected to a gate driver 15b of a scan driving section 15. The scan driving section 15 supplies an on-state voltage and an off-state voltage to the gate driver 15b from a power source circuit 15a via a wire 15c. Then, the gate driver 15b switches a voltage to be applied to each of lines L1 to Lx of the scanning line 5 between the on-state voltage and the off-state voltage so that on/off operation of each of TFTs 8 can be controlled.

Moreover, each of the signal lines 6 is respectively connected to each of readout circuits 17 incorporated in a readout IC 16. In the present embodiment, the readout circuit 17 mainly includes an amplifier circuit 18, a correlated double sampling circuit 19, and the like. In the readout IC 16, an analog multiplexer 21 and an A/D converter 20 are further provided. Note that in FIG. 3, the correlated double sampling circuit 19 is described as CDS.

In the radiation image capturing device 1, when radiation is irradiated through a subject, readout processing of image data D from each radiation detecting element 7 is subsequently carried out. In the present embodiment, electric charges generated and accumulated inside the radiation detecting elements 7 flow out from the radiation detecting elements 7 to the signal lines 6 via the TFTs 8 which were driven to an on-state after an on-state voltage had been applied to the TFTs 8 from the gate driver 15b via the scanning lines 5 in the readout processing.

Then, by the amplifier circuit 18, a voltage value according to the amount of the electric charges which flowed into the circuit via the signal line 6 is outputted from an output side. The correlated double sampling circuit 19 outputs the increased amount of the output value from the amplifier circuit 18 before and after the electric charges flow from each of the radiation detecting elements 7 as the image data D of an analog value to a downstream side.

Then, each piece of the image data D thus outputted is sequentially transmitted to the A/D converter 20 via the analog multiplexer 21, sequentially converted into image data D of a digital value by the A/D converter 20, and outputted to a storage section 23 to be sequentially stored. The readout processing of the image data D is thus carried out.

A controlling section 22 includes a computer including a central processing unit (CPU), a read only memory (ROM), a random access memory (RAM), an input/output interface, and the like connected to each other through a bus, or a field programmable gate array (FPGA) (not shown). Moreover, the controlling section 22 may be configured with a dedicated control circuit.

Moreover, the controlling section 22 controls operation or the like of each functional section of the radiation image capturing device 1 such as controlling the scan driving section 15 or the readout circuit 17 so that the above-mentioned readout process of the image data D is carried out. In addition, as shown in FIG. 3, the storage section 23 including a static RAM (SRAM) or a synchronous dynamic RAM (SDRAM) is connected to the controlling section 22.

Furthermore, in the present embodiment, the above-mentioned antenna device 41 as a wireless communication section is connected to the controlling section 22. Moreover, a battery 24 for supplying necessary power to each functional section such as the scan driving section 15, the readout circuit 17, the storage section 23, the bias supply 14 and the like is connected to the controlling section 22.

Next, other devices in the radiation image capturing system 50 will be explained. Note that in FIG. 1, a case where a portable radiation generation unit 51 is brought into a patient's room R by being mounted on a visiting car 67 or the like is shown as an example. The above-mentioned radiation image capturing device 1 is brought into a patient's room R and is sandwiched between a bed B and body of a patient H or placed to the body of the patient H to be used, as shown in FIG. 1.

The portable radiation generation unit 51 includes a portable radiation source 52 for irradiating radiation to the radiation image capturing device 1 via the body of the patient H, that is, a subject. Moreover, an irradiating direction of radiation, a radiation field of the radiation to be irradiated, or the like of the portable radiation source 52 can be appropriately changed and radiation can be appropriately irradiated to the radiation image capturing device 1 which was sandwiched between the bed B and the body of the patient H or placed to the body of the patient H.

The radiation generation unit 51 can set a tube voltage or a tube current to be applied to the portable radiation source 52 in order to irradiate an appropriate dose of radiation from the portable radiation source 52, or can carry out necessary processing such as setting irradiation time of radiation. The portable radiation generation unit 51 includes an emitting switch 53, and when an operator E such as a radiology technician operates the emitting switch 53, the portable radiation generation unit 51 irradiates radiation from the portable radiation source 52 according to the operation.

In the present embodiment, a portable access point 60 is mounted on the visiting car 67. In the present embodiment, the portable access point 60 can carry out data communication between the radiation image capturing device 1 being a wireless terminal by use of the wireless LAN in a 5 GHz band frequency.

Moreover, in the present embodiment, the portable access point 60 carries out data communication also between a later-described mobile terminal 70 by use of the wireless LAN. That is, in the present embodiment, the portable access point 60 is configured to relay wireless data communication between the radiation image capturing device 1 and the mobile terminal 70.

In the present embodiment, the portable access point 60 is further connected to a console 65 mounted on the visiting car 67 by a cable via a relay device 61 incorporated in the portable radiation generation unit 51 and transmits, for example, the image data D or the like transmitted from the radiation image capturing device 1 to the mobile terminal 70 by a wireless method and to the console 65 via the cable.

In the present embodiment, the mobile terminal 70 and the console 65 include a computer or the like, and a display section 71 and a display section 65a including a cathode ray tube (CRT) or a liquid crystal display (LCD) are respectively provided.

Moreover, an unillustrated wireless communication section is provided to the mobile terminal 70 and the mobile terminal 70 can input an instruction to the mobile terminal 70 or the radiation image capturing device 1 by operation such as touching on a display of the display section 71 by an operator E such as a radiology technician.

In addition, in the present embodiment, the mobile terminal 70 connected to the portable access point 60 by a wireless method functions as a channel determination section for determining a channel CH to be used when data is transmitted or received between the radiation image capturing device 1 being a wireless terminal and the access point 60 by the wireless method.

Hereinafter, an explanation will be given of the determination processing of the channel CH, which is to be used, by the mobile terminal 70 as the channel determination section. Moreover, operation of the radiation image capturing system 50 as a data communication system according to the present embodiment will be explained together.

Figure 4:
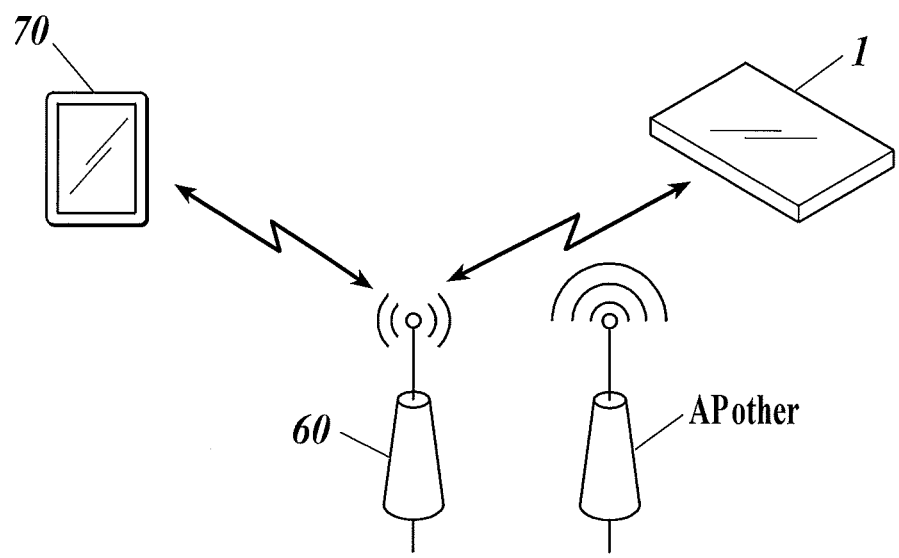
FIG. 4 is an image view showing connection relations or the like in wireless data communication between the radiation image capturing device as a wireless terminal according to the present embodiment and a mobile terminal as an access point and a channel determination section.

Connection relations of wireless data communication between, for example, the radiation image capturing device 1 brought into the patient's room R, the portable access point 60, and the mobile terminal 70 are shown briefly in FIG. 4.

That is, wireless data communication is carried out between the radiation image capturing device 1 and the portable access point 60 and a radio wave transmitted/received between another access point A P other and an unillustrated wireless terminal (that is, for example, a computer, audio equipment, visual equipment, a game machine, or the like) becomes an interfering radio wave for data communication between the radiation image capturing device 1 and the portable access point 60.

Moreover, in the present embodiment, wireless data communication can be carried out between the mobile terminal 70 as the channel determination section (hereinafter referred to as a channel determination section 70) and the portable access point 60. The channel determination section 70 determines the channel CH to be used for wireless transmission/receiving of data between the radiation image capturing device 1 being a wireless terminal and the portable access point 60.

Note that in the present embodiment, data communication is carried out by use of the wireless LAN in a frequency bandwidth of 5 GHz. However, if the band frequency enables the effects of the present invention to be explained later, the band frequency in which the present invention is applied is not limited to the 5 GHz band.

Moreover, in the present embodiment, when the system is started, the channel determination section 70 and the portable access point 60 acknowledges the radio wave environment in a channel for communication (that is, strength of the interfering radio wave or the like) set in the portable access point 60 in a default condition (that is, initial condition).

Then, if it is judged that the radio wave environment is bad, such fact is displayed on the display section 71 of the mobile terminal 70 being the channel determination section 70 (refer to FIG. 1), and when an operator E such as the radiology technician inputs an instruction for execution of instructing the mobile terminal 70 to carry out determination processing of the channel CH to be used, the following determination processing is carried out. However, it is also possible to configure the system to carry out the determination processing without waiting for the input of the instruction for execution.

In the present embodiment, the channel determination section 70 converts the influence rate by the interfering radio wave into a numerical value called a score S, calculates it for each channel CH, selects one channel CH having the smallest score S, and determines the channel CH to be the channel used for wireless data communication between the radiation image capturing device 1 being the wireless terminal and the portable access point 60.

Figure 5:
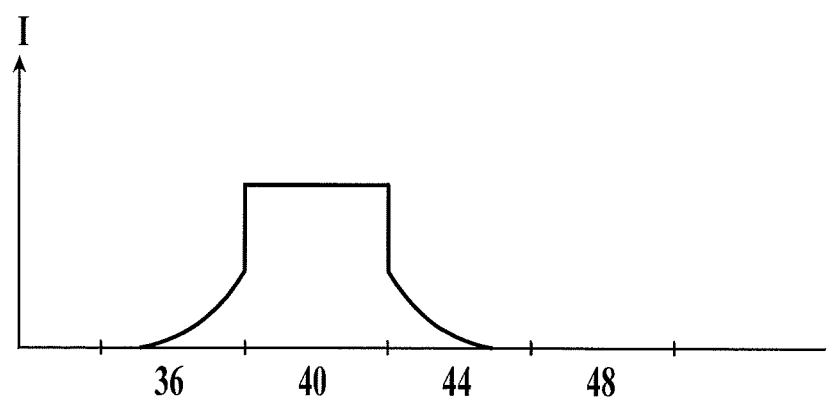
FIG. 5 is a view explaining how radio waves leak out to another channel.

Then, as mentioned above, in a case where, for example, wireless LAN is used in the band frequency of 5 GHz, there is a characteristic that a radio wave leaked out from the used channel CH expands only to the channels adjacent to the channel CH (refer to FIG. 5). The abscissa of FIG. 5 is the channel CH and the ordinate is the strength I of the radio wave. Additionally, FIG. 5 shows that the channel used is channel 40, and the adjacent channels are channel 36 and channel 44. Therefore, in the present embodiment, calculation processing of the score S is carried out by separately calculating a score S($\alpha$) expressing influence rate by an interfering radio wave using the target channel CH and a score S($\beta$) expressing influence rate by an interfering radio wave using channels adjacent to the target channel CH. $\alpha$ is the interfering radio wave using the target channel, and $\beta$ is the interfering radio wave using the channel adjacent to the target channel.

Then, a total of the scores S($\alpha$) and S($\beta$) is calculated as the score S of the channel CH.

First of all, a method to calculate the score S($\alpha$) expressing influence rate by an interfering radio wave using the target channel CH will be explained.

Figure 6:
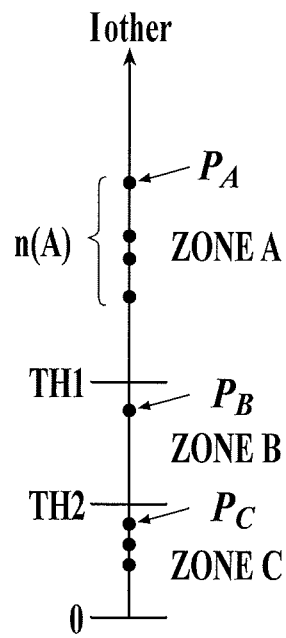
FIG. 6 is a view explaining a plurality of zones or the like for classifying the strength of the interfering radio wave using a target channel.

In this case, as shown in FIG. 6, strength I other of the interfering radio wave, that is, the strength I other of a radio wave transmitted/received between another access point A P other (refer to FIG. 4) using the same channel CH and another wireless terminal, is classified into three zones, A, B, and C.

Then, scores S(A), S(B), and S(C) of each of zones A, B, and C are respectively set so that the value of the score in each zone is higher as transmission/receiving of the data between the radiation image capturing device 1 (wireless terminal) of the radiation image capturing system 50 and the portable access point 60 becomes more difficult when the interfering radio wave having the strength I other of the zone A exists. Subsequently, scores S(A), S(B), and S(C) in each of zones A, B, and C are added to calculate the score S($\alpha$).

First, in a case where the strength I other of the interfering radio wave is as strong as in the zone A shown in FIG. 6, as known well, the portable access point 60 or the like of the present system and the access point A P other of another system recognize the existence of each other and carry out data communication so as not to superimpose each other's communication. Thus, the zone A is equivalent to a first zone where the interfering radio wave is so strong as to allow the portable access point 60 of the present radiation image capturing system 50 and the access point A P other of another system to recognize each other's existence when the strength of the interfering radio wave is divided.

As a result thereof, there is a case where data communication between the radiation image capturing device 1 and the portable access point 60 is often cut off temporarily and communication speed of the data communication is lowered. Therefore, the influence rate is high, but such interfering radio wave does not completely block the data communication between the radiation image capturing device 1 and the portable access point 60.

In the present embodiment, for example, the channel determination section 70 calculates the score S(A) as a numerical value expressing the influence rate of the interfering radio wave of the strength I other belonging to the zone A as follows:

$$S(A)=C_A \times P_A \times a^{n(A)} \quad (1)$$

Here, $C_A$ is a predetermined constant, $P_A$ is a maximum value of the strength I other of a plurality of interfering radio waves belonging to the zone A, a is a constant such as, for example, 10 or the like, n(A) expresses number of access points A P other transmitting interfering radio waves having the strength I other belonging to the zone A (refer to FIG. 6). Moreover, if there is no other access point A P other which transmits the interfering radio wave having the strength I other belonging to the zone A, the maximum value $P_A$ becomes 0 and therefore the score S(A) also becomes 0.

That is, in the present embodiment, the access points A P other of another system in the zone A transmit interfering radio waves having various strength I other belonging to the zone A. However, it is assumed that in the future, there is a possibility that these access points A P other transmit an interfering radio wave having strength $P_A$, which is the maximum value of the strength I other of the interfering radio waves measured in the zone A at this point of time. Then, the influence rate is calculated as the score S(A) in a case where n(A) access points of other access points A P other transmit the interfering radio wave having the strength of the maximum value $P_A$.

Moreover, in a case where the strength I other of the interfering radio wave is weak as in the zone C shown in FIG. 6, the portable access point 60 of the present system and the access point A P other of the other system do not recognize each other's existence unlike the above-mentioned case and the influence by the interfering radio wave can be regarded as noise in the data communication between the radiation image capturing device 1 and the portable access point 60. In other words, the interfering radio wave having the strength I other which is so weak as to be regarded as noise is classified in the zone C. That is, the zone C is equivalent to a second zone, where the strength of the interfering radio wave thereof is weak enough to be regarded as noise.

Then, in the present embodiment, for example, the channel determination section 70 calculates the score S(C) as a numerical value expressing the influence rate of the interfering radio wave belonging to the zone C as follows:

$$S(C)=C_C \times P_C \quad (2)$$

Here, $C_C$ expresses a predetermined constant set to be a small positive value, and $P_C$ expresses a maximum value of the strength I other of a plurality of interfering radio waves belonging to the zone C. Moreover, in this case also, if there is no other access point A P other which transmits the interfering radio wave having the strength I other belonging to the zone C, the maximum value $P_C$ becomes 0 and therefore the score S(C) also becomes 0.

That is, in the present embodiment, no matter how many other access points A P other which transmit the interfering radio wave having the strength I other exist in the zone C, the interfering radio waves transmitted from those other access points are regarded as noises and recognized to not have a great influence on the data communication between the radiation image capturing device 1 and the portable access point 60.

Thus, even if the interfering radio wave whose strength I other belongs to the zone A or the zone C exists, it is possible to transmit and receive data with a wireless method between the radiation image capturing device 1 being a wireless terminal and the portable access point 60.

On the other hand, according to a study by the inventors of the present invention, it was found out that the interfering radio wave belonging to the zone B having a medium strength I other which is weaker than that of the zone A but stronger than that of the zone C, not the interfering radio wave belonging to the zone A of FIG. 6 having a strong strength I other, can greatly influence data communication between the radiation image capturing device 1 and the portable access point 60. The zone B is equivalent to a third zone having a medium strength between the above-mentioned zone A and the zone C.

The reason why the interfering radio wave belonging to the zone B can most greatly influence the data communication between the radiation image capturing device 1 and the portable access point 60 as mentioned above is as follows.

That is, as mentioned above, if there is the other access point A P other which transmits a radio wave having the strength I other belonging to the zone A, that system and the present radiation image capturing system 50 can recognize each other's existence and therefore while the other system is carrying out data communication, the present system can postpone its own data communication. Thus, when data communication is carried out between the radiation image capturing device 1 and the portable access point 60 of the present radiation image capturing system 50, data communication is not interrupted by the other system and therefore a condition where data communication can be carried out is maintained at least during that period of time.

Therefore, even though there are cases where the data communication between the radiation image capturing device 1 and the portable access point 60 is often cut off temporarily and data communication speed is lowered, at least a condition where data communication between the radiation image capturing device 1 and the portable access point 60 is blocked by the interfering radio wave of zone A does not arise.

Moreover, as mentioned above, the interfering radio wave having the strength I other belonging to the zone C has an influence which is recognized only as a noise and in this case also data communication between the radiation image capturing device 1 and the portable access point 60 is not blocked by the interfering radio wave of the zone C.

On the other hand, in a case where there is the other access point A P other which transmits a radio wave having the strength I other of the zone B, there may be a case where the other system cannot recognize the existence of the present radiation image capturing system 50 although the present radiation image capturing system 50 recognizes the existence of the other system. If such a condition arises, the other system keeps transmitting interfering radio waves and there is no timing for the present radiation image capturing system 50 to transmit a radio wave since the other system keeps transmitting the interfering radio waves.

Therefore, according to the present radiation image capturing system 50, in the worst case, data communication between the radiation image capturing device 1 and the portable access point 60 cannot be carried out as long as there is an interfering radio wave having the strength I other of the zone B.

That is, the interfering radio wave having the strength I other belonging to the zone B has a possibility of blocking wireless transmission/receiving of data between the radiation image capturing device 1 being the wireless terminal and the portable access point 60.

Therefore, in the present embodiment, the channel determination section 70 calculates the score S(B) as a numerical value expressing the influence rate of the interfering radio wave belonging to the zone B as follows:

$$S(B)=C_B \times P_B \tag{3}$$

Here, $C_B$ expresses a predetermined constant and $P_B$ expresses a maximum value of the strength I other of a plurality of interfering radio waves belonging to the zone B. Moreover, in the present embodiment, the above-mentioned constant $C_B$ is set to be a large value, such as $10^{10}$. It is also possible to set the constant $C_B$ to be a very large value of, for example, $10^{100}$.

In the present embodiment, the constant $C_B$ is set to be a large value so that in a case where the interfering radio wave having the strength I other belonging to the zone B exists in the target channel CH, a value large enough to prevent the channel CH from being selected is set as the score S(B).

Therefore, in a case where the other access point A P other which transmits an interfering radio wave having the strength I other of the zone B exists, score S(B) becomes a very large value. Therefore, the channel is not practically selected as a channel CH used when wireless transmission/receiving of data is carried out between the radiation image capturing device 1 being a wireless terminal and the portable access point 60.

Note that in this case also, if there is no other access point A P other which transmits the interfering radio wave having the strength I other belonging to the zone B, the maximum value $P_B$ becomes 0 and therefore the score S(B) also becomes 0.

Moreover, excluding the cases where each of the scores S(A), S(B), and S(C) becomes 0, the magnitude relationship between each of the scores S(A), S(B), and S(C) becomes as follows:

$$S(A), S(B) \gg S(C) \tag{4}$$

Moreover, the magnitude relationship between the scores S(A) and S(B) may change depending on the number n(A) of the access points A P other which transmits an interfering radio wave having the strength belonging to the zone A, although the relationship also depends on how the constant $C_B$ is set.

Moreover, threshold values TH1 and TH2 (refer to FIG. 6 or FIG. 7) concerning the strength I other for classifying the zones A to C are appropriately set according to the above-mentioned characteristics of each zone.

In the present embodiment, the channel determination section 70 adds the scores S(A), S(B), and S(C) calculated in terms of each of the zones A, B, and C as in the following equation (5) to calculate the score S(α) expressing the influence rate of the interfering radio wave using the target channel CH:

$$S(\alpha)=S(A)+S(B)+S(C) \tag{5}$$

Therefore, if there is no interfering radio wave using the target channel CH, the scores S(A), S(B), and S(C) of each of the zones A, B, and C become 0 and therefore $S(\alpha)$ also becomes 0. Moreover, if there exists only the interfering radio wave having the strength I other belonging to the zone C and an interfering radio wave having the strength I other belonging to the zone A or the zone B does not exist, $S(\alpha)=S(C)$ and the score $S(\alpha)$ does not have a large value.

However, if there exists the interfering radio wave having the strength I other of the zone A, the value of the score $S(\alpha)$ becomes larger for the value of the score $S(A)$ in proportion to the number of the interfering radio waves. Moreover, if there exists the interfering radio wave having the strength I other of the zone B, score $S(B)$ having a very large value is added and therefore the score $S(\alpha)$ becomes a very large value.

Therefore, if it is configured that the score $S(\alpha)$ (that is, the scores $S(A)$, $S(B)$, and $S(C)$) is calculated as mentioned above, the value of the score $S(\alpha)$ can be varied to correspond to the degree of the influence rate of the interfering radio wave to the data communication between the radiation image capturing device 1 and the portable access point 60.

That is, in a case where the influence rate of the interfering radio wave to the data communication between the radiation image capturing device 1 and the portable access point 60 may be so large as to have a possibility of not allowing data communication between the radiation image capturing device 1 being a wireless terminal and the portable access point 60 (the case of zone B), the score SW becomes very large. Moreover, in a case where the influence rate is not so large as to completely prevent the data communication but is large enough to often cut off the data communication temporarily (the case of zone A), the score $S(\alpha)$ also becomes large. However, in a case where the influence rate is small enough to be recognized as a noise (the case of zone C), the score $S(\alpha)$ can be varied so that the score $S(\alpha)$ becomes a small value.

Note that although attention was paid only to the strength I other of the interfering radio wave in FIG. 6, as understood from the above consideration, if a strength I self of a radio wave transmitted from the portable access point 60 of the present radiation image capturing system 50 becomes stronger to a certain degree, the other access point A P other transmitting the interfering radio wave having the strength I other of the zone B recognizes the existence of the radiation image capturing system 50. Then, while the radiation image capturing system 50 carries out data communication, the other system postpones its data communication and therefore such interfering radio wave does not belong to the zone B any more but belongs to the zone A.

Figure 7:
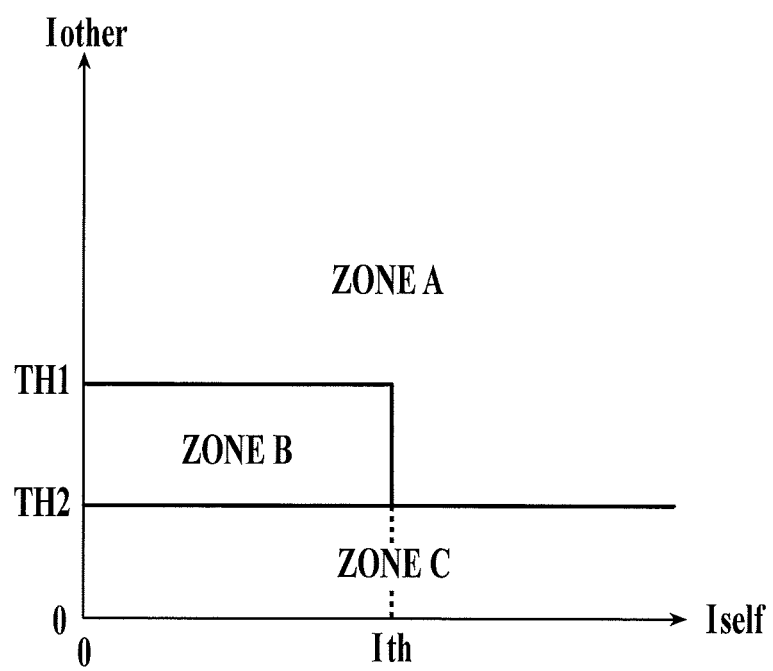
FIG. 7 is a view explaining a relationship or the like of a plurality of zones or the like for classifying the strength of the interfering radio wave using a target channel and the strength of the radio wave of the own system.

That is, as shown in FIG. 7, in a case where the strength I self of the radio wave used for the data communication between the radiation image capturing device 1 and the portable access point 60 (hereinafter referred to as the strength I self of the radio wave of the radiation image capturing system 50) is on the abscissa, if the strength I self of the radio wave of the radiation image capturing system 50 is smaller than a predetermined strength Ith, the other access point A P other transmitting an interfering radio wave having a strength of I other of the zone B cannot recognize the existence of the radiation image capturing system 50. Therefore, in the case of such interfering radio wave, the radio wave is regarded as the interfering radio wave belonging to the zone B shown in FIG. 6 and the score $S(B)$ is calculated.

However, in a case where the strength I self of the radio wave of the radiation image capturing system 50 becomes larger and becomes equal to or larger than the predetermined strength of Ith, the other access point A P other transmitting an interfering radio wave having a strength I other of the zone B recognizes the existence of the radiation image capturing system 50 on this side and the other system postpones its data communication while the radiation image capturing system 50 carries out the data communication. Therefore, in a case where the strength I self of the radiation image capturing system 50 is equal to or larger than the predetermined strength Ith, the zone B does not exist any more and the zone becomes a zone similar to the zone A, and according to the above equation (1), the score $S(A)$ is calculated.

Therefore, for example, as shown in FIG. 7, the channel determination section 70 includes in advance the relationship between the strength I other of the interfering radio wave transmitted by the other access point A P other and the strength I self of the radio wave of the radiation image capturing system 50. That is, it is configured that in response to the strength I self of the radio wave of the radiation image capturing system 50 (in other words, depending on whether or not the strength I self of the radio wave of the radiation image capturing system 50 is less than the predetermined strength Ith or is equal to or more than the predetermined strength Ith), application is switched between the case where the strength I other of the interfering radio wave transmitted by the other access point A P other is classified into the three zones of A to C and a case where the strength I other is classified into either the zone A or the zone C and the score $S(\alpha)$ is calculated.

Next, a method for calculating the score $S(\beta)$ expressing the influence rate of the interfering radio wave using a channel adjacent to the target channel CH will be explained.

Figure 8:
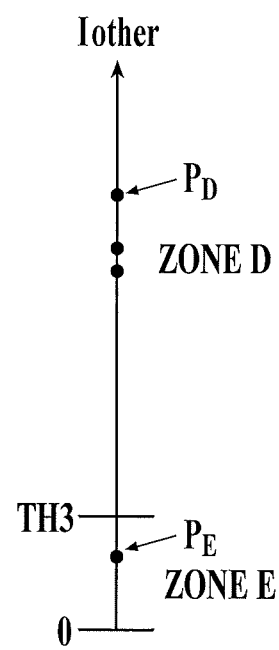
FIG. 8 is a view explaining plurality of zones or the like for classifying the strength of the interfering radio wave using channels next to a target channel.

In this case also, similarly to the case shown in FIG. 6 or FIG. 7, the strength I other of the interfering radio wave, that is, the strength I other of the radio wave transmitted and received between the other access point A P other (refer to FIG. 4) using a channel adjacent to the target channel CH and another wireless terminal is classified into zone D and zone E, setting a threshold value TH3 as a border, as shown in FIG. 8.

First, an explanation will be given of the zone E, where the strength I other of the interfering radio wave is weak. In this case, the influence by the interfering radio wave can be regarded as a noise that superimposes the data communication between the radiation image capturing device 1 and the portable access point 60. In other words, an interfering radio wave having the strength I other which is so weak as to be regarded as a noise is classified into the zone E.

Here, in the present embodiment, the channel determination section 70 calculates a score $S(E)$ as a numerical value expressing the influence rate of the interfering radio wave belonging to the zone E similarly to, for example, the score $S(C)$ as a numerical value expressing the influence rate of the interfering radio wave belonging to the zone C as follows:

$$S(E)=C_E \times P_E \qquad (6)$$

In this case also, $C_E$ expresses a predetermined constant set as a small positive value, and $P_E$ expresses a maximum value of the strength I other of a plurality of interfering radio waves belonging to the zone E. Moreover, in this case also, if there is no other access point A P other which transmits the interfering radio wave having the strength I other belonging to the zone E, the maximum value $P_E$ becomes 0 and therefore the score $S(E)$ also becomes 0.

An explanation will be given of the zone D, where the strength I other of the interfering radio wave is weak. In a case where the interfering radio wave does not use the target channel CH but uses a channel adjacent thereto, even if the strength I other of the interfering radio wave is strong, neither the system, to which the access point A P other transmitting the interfering radio wave belongs, nor the radiation image capturing system 50 postpones data communication while either of the systems is carrying out the data communication.

In this case, the interfering radio wave of the zone D is the interfering radio wave using an adjacent channel which leaked out to the target channel CH and therefore unless an extraordinarily strong interfering radio wave is used by the adjacent channel, the radio wave leaked out to the target channel CH is generally not so strong as not to allow data communication. However, the strength I other is too strong to be regarded as noise like the interfering radio wave of the zone E and therefore it can be said that the environment is not preferable for data communication.

Therefore, in the present embodiment, the channel determination section 70 calculates a score S(D) as a numerical value expressing the influence rate of the interfering radio wave belonging to the zone D similarly to, for example, the score S(C) and the score S(E) as follows:

$$S(D)=C_D \times P_D \tag{7}$$

In this case, the constant $C_D$ is set to have a larger value than the above-mentioned constant $C_C$ or the constant $C_E$. Note that $P_D$ expresses a maximum value of the strength I other of a plurality of interfering radio waves belonging to the zone D. Moreover, in this case also, if there is no other access point AP other which transmits the interfering radio wave having the strength I other belonging to the zone D, the maximum value $P_D$ becomes 0 and therefore the score S(D) also becomes 0.

Note that in the above-mentioned case, excluding the cases where each of the scores S(D) and S(E) becomes 0, the magnitude relationship between each of the scores S(D) and S(E) becomes as follows:

$$S(D) \gg S(E) \tag{8}$$

Moreover, the threshold value TH3 (refer to FIG. 8) concerning the strength I other for classifying the zones D and E is appropriately set according to the above-mentioned characteristics of each zone.

In addition, the relationship shown in FIG. 8, unlike the relationship shown in FIG. 7, does not vary depending on the strength I self of the radio wave of the radiation image capturing system 50 (that is, the strength I self of the radio wave used for the data communication between the radiation image capturing device 1 and the portable access point 60 in the radiation image capturing system 50).

In the present embodiment, the channel determination section 70 adds the scores S(D) and S(E) calculated in terms of each of the zones D and E as in the following equation (9) to calculate the score S(β) expressing the influence rate of the interfering radio wave using the channel adjacent to the target channel CH:

$$S(\beta)=S(D)+S(E) \tag{9}$$

Therefore, if there is no interfering radio wave using the channel adjacent to the target channel CH, the scores S(D) and S(E) of each of the zones D and E become 0 and therefore S(β) also becomes 0. Moreover, if there exists only the interfering radio wave having the strength I other belonging to the zone E and the interfering radio wave having the strength I other belonging to the zone D does not exist, the result is S(β)=S(E), the interfering radio wave can be considered to be noise, and the score S(β) does not have so large a value.

However, if there is an interfering radio wave having the strength I other of the zone D, the radio wave is too strong to be called noise and although it is not so strong as not to allow data communication, the environment is not preferable for data communication and therefore the value of the score S(β) becomes larger in the value of the score S(D).

Thus, according to the above-mentioned configuration which calculates the score S(β) (that is, scores S(D) and S(E)), it becomes possible to vary the size of the score S(β) in order to correspond with the influence rate of the interfering radio wave using a channel adjacent to the target channel CH applied to data communication between the radiation image capturing device 1 and the portable access point 60.

Note that in a case where the channel adjacent to the target channel CH exists on both the higher frequency side and the lower frequency side of the target channel CH, the score S(β) is calculated as mentioned above for both of the adjacent channels respectively. Hereinafter, the score S(β) expressing the influence rate of the interfering radio waves using channels which are adjacent to the target channel CH on the higher and lower sides thereof will be respectively expressed as a score $S(\beta)_{high}$ and a score $S(\beta)_{low}$.

The channel determination section 70 adds the scores S(α), $S(\beta)_{high}$ and $S(\beta)_{low}$ calculated as above according to the following equation (10) to calculate the score S, a numerical value expressing the influence rate by the interfering radio waves to the target channel CH.

$$S=S(\alpha)+S(\beta)_{high}+S(\beta)_{low} \tag{10}$$

The channel determination section 70 carries out the above-mentioned calculation processing of the score S for all of a plurality of channels CH which can be used for wireless data communication between the radiation image capturing device 1 being a wireless terminal and the portable access point 60 while changing the channel CH. Then, the channel determination section 70 extracts the lowest score S from the scores S calculated for each of the channels CH, selects a channel CH corresponding to the score S, and determines the channel to be the channel CH used for data communication between the radiation image capturing device 1 and the portable access point 60.

As described above, according to the data communication system according to the present embodiment, calculation processing of the score S is carried out for each and every of a plurality of channels CH which can be used for wireless data communication between a wireless terminal (that is, the radiation image capturing device 1 according to the above-mentioned embodiment) and the portable access point 60 and a channel CH having the lowest score S thus calculated is determined to be the channel CH used when wireless transmission/receiving of data between the wireless terminal and the portable access point 60 is carried out.

As mentioned above, the score S, in other words, the score S(α) and the score (β) (that is, the scores S(A) to S(E)) become larger when the influence rate of the interfering radio wave used by the target channel CH or a channel adjacent thereto becomes larger and the scores become smaller when the influence rate becomes smaller.

Therefore, by determining a channel CH having the smallest score S thus calculated to be the channel CH used for data communication between the wireless terminal and the portable access point 60, it becomes possible to accurately select a channel CH for communication which is least influenced by the interfering radio wave used by the other system when data communication is carried out between the wireless terminal and the portable access point 60. Therefore, it becomes possible to carry out data communication between the wireless terminal and the portable access point 60 in a condition where the communication is least influenced by the interfering radio wave.

Moreover, according to the radiation image capturing system 50 utilizing the data communication system according to the present embodiment, it becomes possible to carry out data communication between the radiation image capturing device 1 being the wireless terminal and the portable access point 60 in a condition where the communication is least influenced by the interfering radio wave used by the other system.

Therefore, it becomes possible to transmit necessary data or a signal from, for example, the mobile terminal 70 or the console 65 (refer to FIG. 1) to the radiation image capturing device 1 in a condition where such transmission is least influenced by the interfering radio wave and to appropriately operate the radiation image capturing device 1. Moreover, at the same time, it becomes possible to transmit data such as image data from the radiation image capturing device 1 to the console 65 or the mobile terminal 70 in a condition where such transmission is least influenced by the interfering radio wave.

As a result, it becomes possible to preferably carry out data communication between each device of the radiation image capturing system 50, to accurately carry out capturing of a radiation image, and to maintain and improve operability of the radiation image capturing system 50.

Note that in the present embodiment, a case where the mobile terminal 70 is used as the channel determination section was explained. However, it is also possible to configure the system by use of the console 65 as the channel determination section instead of the mobile terminal 70.

Moreover, it is needless to say that the present invention is not limited to the above-described embodiment or the like and can be appropriately modified without departing from the scope and spirit of the present invention.

The present application is based on Japanese Patent Application No. 2012-096290 filed on Apr. 20, 2012 to the Japanese Patent Office, which shall be a basis for correcting mistranslations.

What is claimed is:

1. A data communication system comprising:
   a wireless terminal including a wireless communication section which carries out wireless transmission/receiving of data;
   an access point which carries out wireless transmission/receiving of the data with the wireless communication section of the wireless terminal; and
   a channel determination section which is connected to the access point and which determines a channel to be used when carrying out the wireless transmission/receiving of the data between the wireless terminal and the access point,
   wherein the channel determination section:
     carries out calculation processing for quantifying the influence rate of an interfering radio wave and calculating the influence rate as a score for each channel among a plurality of usable channels by switching to a target channel among the plurality of usable channels, for a case where data communication is carried out by use of a radio wave of the target channel, on the basis of the influence rate of the interfering radio wave in the target channel, and determines a channel having the smallest calculated score to be a channel used for wireless transmission/receiving of the data between the wireless terminal and the access point, and
     classifies the influence rate by the interfering radio wave in the target channel into a first zone where strength of the interfering radio wave is strong enough to cause the access point of the data communication system and an access point of another system to recognize existence of each other, a second zone where the strength of the interfering radio wave is weak enough to be regarded as noise, and a third zone where the strength is intermediate between the first zone and the second zone, sets a score in each of the first zone, the second zone, and the third zone so that the value of the score is higher as transmission/receiving of the data between the wireless terminal and the access point of the data communication system becomes more difficult when the interfering radio wave having the strength of each zone exists, adds the scores of each zone, and calculates the score for each channel among the plurality of usable channels.

2. The data communication system of claim 1, wherein in terms of the third zone where the strength is intermediate, in a case where there exists the interfering radio wave with the strength of the third zone in the target channel, a value too large to select the target channel is set as the score of the third zone.

3. The data communication system of claim 1, wherein the channel determination section carries out calculation processing for quantifying the influence rate of the interfering radio wave on the basis of not only the influence rate of the interfering radio wave of the target channel but also the influence rate of the interfering radio wave of the channel adjacent to the target channel for a case where data communication is carried out by use of the radio wave of the target channel and calculating the influence rate of the interfering radio wave as a score.

4. The data communication system of claim 1, wherein the channel determination section calculates the score of each of the zones assuming that the interfering radio wave having the strength belonging to the third zone as the interfering radio wave having the strength belonging to the first zone in a case where the radio wave transmitted by the access point of the data communication system is equal to or stronger than a predetermined strength.

5. A radiation image capturing system comprising:
   a data communication system comprising:
     a wireless terminal including a radiation image capturing device and a wireless communication section which carries out wireless transmission/receiving of data, wherein the radiation image capturing device comprises a plurality of radiation detecting elements aligned at least two-dimensionally;
     an access point which carries out wireless transmission/receiving of the data with the wireless communication section of the wireless terminal; and
     a channel determination section which is connected to the access point and which determines a channel to be used when carrying out the wireless transmission/receiving of the data between the wireless terminal and the access point, wherein the channel determination section comprises a mobile terminal or a console including a computer,
   wherein the channel determination section:
     carries out calculation processing for quantifying the influence rate of an interfering radio wave and calculating the influence rate as a score for each channel among a plurality of usable channels by switching to a target channel among the plurality of usable channels, for a case where data communication is carried out by use of a radio wave of the target channel, on the basis of the influence rate of the interfering radio wave in the target channel, and determines a channel having the smallest calculated score to be a channel used for wireless transmission/receiving of the data between the wireless terminal and the access point, and
     classifies the influence rate by the interfering radio wave in the target channel into a first zone where strength of the interfering radio wave is strong enough to cause the access point of the data communication system and an access point of another system to recognize existence of each other, a second zone where the strength of the interfering radio wave is weak enough to be regarded as noise, and a third zone where the strength is intermediate between the first zone and the second zone, sets a score in each of the first zone, the second zone, and the third zone so that the value of the score is higher as transmission/receiving of the data between the wireless terminal and the access point of the data communication system becomes more difficult when the interfering radio wave having the strength of each zone exists, adds the scores of each zone, and calculates the score for each channel among the plurality of usable channels.

* * * * *